US008426671B2

(12) United States Patent
Steffen et al.

(10) Patent No.: US 8,426,671 B2
(45) Date of Patent: Apr. 23, 2013

(54) LIQUID MANAGEMENT LAYER FOR PERSONAL CARE ABSORBENT ARTICLES

(75) Inventors: John F. Steffen, Denver, NC (US); Pierre D. Grondin, Mooresville, NC (US); Ralph A. Moody, III, Mooresville, NC (US)

(73) Assignee: Polymer Group, Inc., Charlotte, NC (US)

( * ) Notice: Subject to any disclaimer, the term of this patent is extended or adjusted under 35 U.S.C. 154(b) by 308 days.

(21) Appl. No.: 13/026,059

(22) Filed: Feb. 11, 2011

(65) Prior Publication Data

US 2012/0209233 A1    Aug. 16, 2012

(51) Int. Cl.
*A61F 13/531* (2006.01)
*A61F 13/53* (2006.01)

(52) U.S. Cl.
USPC .......................................... 604/370; 604/367

(58) Field of Classification Search ................... 604/370, 604/367
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,949,130 A | 4/1976 | Sabee et al. | |
| 4,340,563 A | 7/1982 | Appel et al. | |
| 5,292,239 A | 3/1994 | Zeldin et al. | |
| 5,364,382 A | 11/1994 | Latimer et al. | |
| 5,429,629 A | 7/1995 | Latimer et al. | |
| 5,486,166 A | 1/1996 | Bishop et al. | |
| 5,490,846 A | 2/1996 | Ellis et al. | |
| 5,522,810 A | 6/1996 | Allen, Jr. et al. | |
| 5,562,650 A | 10/1996 | Everett et al. | |

(Continued)

FOREIGN PATENT DOCUMENTS

EP    0670154 A2    6/1995
WO    9615748 A2    5/1996

OTHER PUBLICATIONS

International Search Report and Written Opinion, Appln. No. PCT/US12/23133, Jun. 8, 2012 (10 pages).

*Primary Examiner* — Susan Su
(74) *Attorney, Agent, or Firm* — Kilyk & Bowersox, P.L.L.C.; Valerie Calloway

(57) ABSTRACT

A liquid management layer constructed from large diameter uncrimped fibers in the form of a spunbond nonwoven web is described. Embodiments of the liquid management layer can include a plurality of thermoplastic fibers in the form of a spunbond nonwoven web where the plurality of thermoplastic fibers are randomly oriented and uncrimped, where the liquid management layer has a maximum void volume of 25 cc/g and a web density of at least 0.05 g/cc, where the liquid management layer has a maximum thickness of 1.5 mm, a basis weight of at least 30 g/m² and a rewet value of less than 0.4 g according to test method WSP 70.8, and where the liquid management layer has an average fiber diameter of at least 40 microns based on the number of thermoplastic fibers in the liquid management layer and where less than 10% by count of the plurality of thermoplastic fibers in the liquid management layer have an absolute fiber diameter less than 30 microns. Additional embodiments of the invention include a personal care absorbent article incorporating the liquid management layer over an absorbent core.

20 Claims, 1 Drawing Sheet

U.S. PATENT DOCUMENTS

| | | |
|---|---|---|
| 5,569,226 A | 10/1996 | Cohen et al. |
| 5,643,653 A | 7/1997 | Griesbach, III et al. |
| 5,649,916 A | 7/1997 | DiPalma et al. |
| 5,669,895 A | 9/1997 | Murakami et al. |
| 5,714,256 A | 2/1998 | DeLucia et al. |
| 5,874,160 A | 2/1999 | Keck |
| 5,879,343 A | 3/1999 | Dodge, II et al. |
| 5,891,120 A | 4/1999 | Chmielewski |
| 5,931,823 A | 8/1999 | Stokes et al. |
| 5,994,615 A | 11/1999 | Dodge, II et al. |
| 6,096,015 A | 8/2000 | Yeo et al. |
| 6,245,961 B1 | 6/2001 | Roxendal et al. |
| 6,294,710 B1 | 9/2001 | Schmidt et al. |
| 6,417,427 B1 | 7/2002 | Roxendal et al. |
| 6,511,566 B1 | 1/2003 | Wessel et al. |
| 6,518,479 B1 | 2/2003 | Graef et al. |
| 6,610,039 B1 | 8/2003 | Wilhelm et al. |
| 6,613,704 B1 | 9/2003 | Arnold et al. |
| 6,660,902 B2 | 12/2003 | Widlund et al. |
| 6,689,242 B2 | 2/2004 | Bodaghi |
| 6,689,934 B2 | 2/2004 | Dodge, II et al. |
| 6,709,623 B2 | 3/2004 | Haynes et al. |
| 6,740,792 B2 | 5/2004 | Waldroup et al. |
| 7,323,072 B2 | 1/2008 | Engelhart et al. |
| 7,807,591 B2 | 10/2010 | Fox et al. |
| 2003/0068947 A1* | 4/2003 | Marmon et al. ............... 442/164 |
| 2003/0120231 A1 | 6/2003 | Wang et al. |
| 2004/0041307 A1* | 3/2004 | Topolkaraev et al. ........ 264/555 |
| 2004/0077247 A1 | 4/2004 | Schmidt et al. |
| 2005/0241745 A1 | 11/2005 | Bansal |
| 2010/0312212 A1 | 12/2010 | Bond et al. |

\* cited by examiner

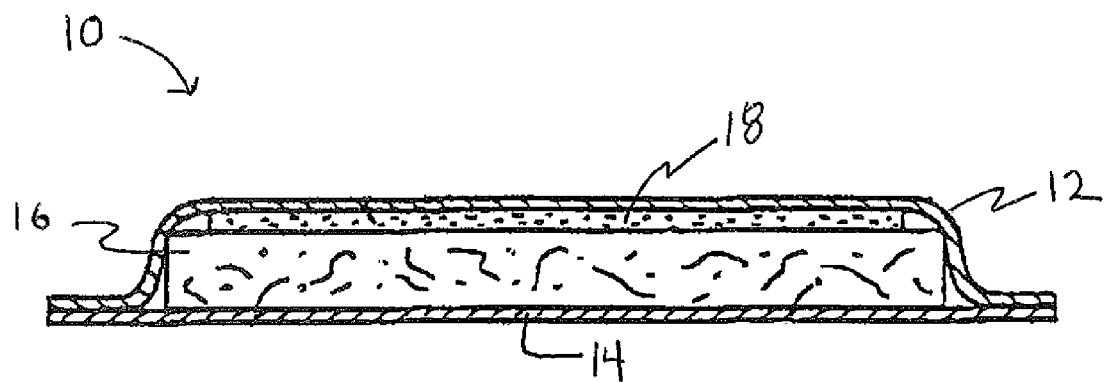

LIQUID MANAGEMENT LAYER FOR PERSONAL CARE ABSORBENT ARTICLES

FIELD OF THE INVENTION

The present invention is related to fibrous nonwoven webs which are useful as a liquid management layer in a personal care absorbent article. More specifically, the present invention relates to a liquid management layer in the form of a large denier nonwoven spunbond web that exhibits a unique combination of characteristics that provide for the rapid intake of multiple insults and distribution of body exudates into an absorbent portion of a personal care absorbent article.

BACKGROUND OF THE INVENTION

Personal care absorbent articles such as diapers, training pants, incontinence devices, feminine hygiene products, and the like are designed to absorb body liquids including blood, urine, menses and feces. In certain instances, these products should be able to quickly absorb relatively large quantities of liquid, urine being an example, and still keep the wearer as dry and comfortable as possible. Typically, such personal care absorbent products include a liquid permeable top sheet, a bottom sheet, and an absorbent core disposed between the top sheet and the bottom sheet. The top sheet is usually made from some type of fibrous permeable nonwoven web such as a bonded carded web or a spunbond web. The bottom sheet typically is made from some type of material or laminate which is liquid impervious, and optionally, breathable.

The absorbent core is usually made from wood pulp fibers also referred to as "fluff" and can optionally include superabsorbent particles which are designed to absorb many times their own weight in liquid. When a child or adult urinates, the urine passes through the top sheet and is absorbed into the absorbent core below. A problem with the absorbent cores is that they are not very effective at quickly channeling liquid away to more remote parts of the absorbent structure. As a result, at least a part of the liquid retained in the core may wick back to the top sheet which is usually in contact with the wearer's skin. This urine-soaked material is at the very least uncomfortable, inhibits air flow to the skin and may possibly exacerbate any skin conditions which are present. Further, liquid not contained by the absorbent core or liquid management layer presents a higher risk of leakage outside the personal care absorbent article.

Attempts have been made to alleviate these problems by placing one or more additional layers of materials between the top sheet and the absorbent core. These materials have been referred to as a liquid management layer, transfer layer, separator layer, surge layer, fluid acquisition and distribution layer, as well as other names (collectively referred to as "liquid management layer"). The function of the liquid management layer is to take up the liquid delivered to it through the top sheet and then transfer the liquid to the absorbent core. Ideally, such a liquid management layer would readily take in liquid to get it away from the skin. The liquid management layer would give up the same liquid to other components in the personal care absorbent product and would be able to separate the skin and top sheet from the rest of the absorbent system. Lastly, the liquid management layer would be able to maintain the separation under a variety of conditions.

Current liquid management layers are able to receive considerable amounts of liquids, move the liquids away from the skin of the wearer, distribute the liquid through and across the liquid management layer, and transfer the liquid to the absorbent core. Typical liquid management layers utilize high loft materials exhibiting high void volumes. For example, U.S. Pat. No. 5,846,166 to Bishop, et al. describes a surge layer for a personal care absorbent article where the material has a void volume ranging from about 80 cc/g to about 117 cc/g. Similarly U.S. Pat. No. 5,490,846 to Ellis, et al. describes a material with a void volume ranging from 40 cc/g to about 60 cc/g. The trend has been to use high loft materials with high void volumes to provide a large space for liquid to be stored temporarily as the liquid is transferred and absorbed by the absorbent core. Often these materials utilize crimped fibers to increase loft and void volumes of the materials. For example, U.S. Pat. No. 6,096,015 to Yeo, et al. discloses a material for a separator layer with fibers of at least 28 microns and discloses that the fibers of the separator layer have a minimum of five crimps per extended inch. While, Yeo, et al. discloses two comparative examples which utilize uncrimped fibers; however, these materials appear to have void volumes greater than 25 cc/g.

One challenge with the high loft materials is compressibility. When the high loft material is placed under load either by the weight of the wearer or in storage, the pore structure of the material changes due to its compressibility. As the pore structure changes under load, the performance of the material changes. Some have used a mixture of relatively large fiber sizes and small fiber sizes to reduce compressibility of the liquid management layer. For example, U.S. Pat. No. 5,364,382 to Latimer, et al. describes using larger, stiffer fibers to provide resiliency and using smaller fibers to increase the available surface area in the material. These types of materials typically have a large number of high loft compressible fibers and exhibit high void volumes. Another liquid management layer is disclosed in U.S. Pat. No. 5,522,810 to Allen, Jr., et al. which describes a compressively resistant and resilient fibrous nonwoven web for use as a liquid management layer that is at least 2.5 mm thick. While this material is compressively resistant, it adds to the overall bulk of the personal care absorbent article.

Another issue with high void volume liquid management layers is the volume they occupy while in bulk form on a roll during storage or transportation prior to being assembled as part of a personal care absorbent article. This is because these high loft materials have a tendency to collapse in a non-reversible way when wound on the roll if the winding tension is too high. Further, in view of using a relatively low winding tension and the thickness of these high loft materials, for rolls of equal diameters, the roll of high void volume liquid management material can have a shorter length of material per roll than a roll of a thinner material. These shorter rolls lead to more frequent roll changes, more waste, and more frequent material splices during the manufacturing process which, in turn, cause delays in production of the personal care absorbent articles.

There is a need for a resistant and resilient liquid management layer which is thinner than that currently realized, which does not add to the bulk of the personal care absorbent article, and yet provides adequate separation between the absorbent core and the top sheet against the surface of the wearer upon multiple insults. Further, there remains a need in the absorbent personal hygiene field for a liquid management layer that maintains its pore structure while under load and can be produced relatively economically compared to carded materials, while still providing necessary performance features for use as a liquid management layer. Many of the materials discussed above are high loft compressible materials or they are thick resilient materials. A proposed solution might be to simply make the materials thinner. Simply making a material thinner can have significant adverse effects upon performance. Therefore, unique properties must be combined to provide a thinner, compression resistant liquid management layer that still meets the performance requirements for a liquid management layer in a personal care absorbent article. The present invention is directed to such a liquid management layer as will become more apparent from the following description, drawing, and claims.

SUMMARY OF THE INVENTION

The present invention is directed to an liquid management layer that utilizes a spunbond web made of large denier fibers that is substantially uncompressible and exhibits void volumes of 25 cc/g or less and high permeability while meeting performance standards for use as a liquid management layer.

In some embodiments, the present invention can include a liquid management layer for a personal care absorbent article, the liquid management layer comprising a plurality of thermoplastic fibers in the form of a spunbond nonwoven web, where the plurality of thermoplastic fibers are randomly oriented and uncrimped, where the liquid management layer has a maximum void volume of 25 cc/g and a web density of at least 0.05 g/cc, where the liquid management layer has a maximum thickness of 1.5 mm, a basis weight of at least 30 g/m$^2$ and a rewet value of less than 0.4 g according to test method WSP 70.8, and where the liquid management layer has an average fiber diameter of at least 40 microns based on the number of thermoplastic fibers in the liquid management layer and where less than 10% by count of the plurality of thermoplastic fibers in the liquid management layer have an absolute fiber diameter less than 30 microns.

In further embodiment the liquid management layer can exhibit a maximum compressibility of 30%. The liquid management layer may include fibers that comprise polypropylene, and where all of the fibers in the liquid management layer are in the spunbond nonwoven web. Further, the liquid management layer can exhibit a basis weight between about 30 g/m$^2$ to about 100 g/m$^2$. In some embodiments, the fibers can exhibit an average fiber diameter ranging from about 40 to about 80 microns. In additional embodiment, the average fiber diameter can be at least 45 microns. In still further embodiments, the average fiber diameter can be at least 55 microns. The spunbond nonwoven web can be stabilized by thermal point bonding. In some embodiments, the liquid management layer can exhibit a permeability factor of at least 11. In additional embodiments, the liquid management layer can include less than 5% by count of the plurality of thermoplastic fibers in the liquid management layer that have an absolute fiber diameter less than 30 microns. Still further, embodiments of the liquid management layer can include at least 95% of the plurality of thermoplastic fibers in the liquid management layer that have an absolute fiber diameter of at least 30 microns. The liquid management layer can include fibers that comprise polypropylene, and the liquid management layer can exhibit a basis weight at least 40 g/m$^2$ and can be stabilized by thermal point bonding, and the liquid management layer can exhibits a maximum compressibility of 30% and a permeability factor of at least 11. In additional embodiments, the liquid management layer can have an average fiber diameter that is at least 55 microns, the fibers can comprise polypropylene, the liquid management layer can exhibit a basis weight of at least 40 g/m$^2$ and can be stabilized by thermal point bonding, and where the liquid management layer can exhibit a maximum compressibility of 30% and a permeability factor of 11 or greater.

Embodiments of the present invention can also include a personal care absorbent article comprising a bottom sheet, a liquid management layer, and an absorbent core positioned between the liquid management layer and the bottom sheet, where the liquid management layer comprises a plurality of thermoplastic fibers in the form of a spunbond nonwoven web, where the plurality of thermoplastic fibers are randomly oriented and uncrimped, where the liquid management layer has a maximum void volume of 25 cc/g and a web density of at least 0.05 g/cc, where the liquid management layer has a maximum thickness of 1.5 mm, a basis weight of at least 30 g/m$^2$ and a rewet value of less than 0.4 g according to test method WSP 70.8, and where the liquid management layer has an average fiber diameter of at least 40 microns based on the number of thermoplastic fibers in the liquid management layer and where less than 10% by count of the plurality of thermoplastic fibers in the liquid management layer have an absolute fiber diameter less than 30 microns.

Further, the personal care absorbent article can comprise a top sheet, where the liquid management layer is positioned between the top sheet and absorbent core. In some embodiments, the personal care absorbent can have a average fiber diameter is at least 45 microns. In other embodiments, the personal care absorbent article can have an average fiber diameter that is at least 55 microns. Still further, the personal care absorbent article can have less than 5% of the plurality of thermoplastic fibers in the liquid management layer that have an absolute fiber diameter less than 30 microns. In additional embodiment, the personal care absorbent article can have at least 95% of the plurality of thermoplastic fibers in the liquid management layer with an absolute fiber diameter of at least 30 microns. The personal care absorbent article can include fibers that comprise polypropylene, where the liquid management layer can exhibit a basis weight at least 40 g/m$^2$ and can be stabilized by thermal point bonding, and where the liquid management layer can exhibit a maximum compressibility of 30% and a permeability factor of at least 11.

Still further, in some embodiments, the present invention can include a liquid management layer for a personal care absorbent article where the liquid management layer comprises a spunbond nonwoven web comprising a plurality of thermoplastic fibers and having a total fiber content, where the plurality of thermoplastic fibers are randomly oriented and uncrimped, where the liquid management layer has a maximum void volume of 25 cc/g and a web density of at least 0.05 g/cc, where the liquid management layer has a maximum thickness of 1.5 mm, a basis weight of at least 30 g/m$^2$ and a rewet value of less than 0.4 g according to test method WSP 70.8, and wherein the plurality of thermoplastic fibers comprise at least 60% by weight of the total fiber content of the spunbond nonwoven web and the plurality of thermoplastic fibers have an average diameter of at least 40 microns (μm), wherein less than 10% of the plurality of thermoplastic fibers in the spunbond nonwoven web have an absolute diameter less than 30 microns.

BRIEF DESCRIPTION OF THE DRAWING

FIG. 1 is a cross-sectional view of a personal care absorbent article in accordance with an embodiment of the invention.

DETAILED DESCRIPTION OF EMBODIMENTS OF THE INVENTION

The present invention is directed to a liquid management layer for personal care absorbent articles such as diapers, training pants, incontinence devices, and feminine hygiene products. With reference to FIG. 1 there is shown a personal care absorbent article represented generally by the reference numeral 10. The present invention will be described in conjunction with this particular embodiment; however, this embodiment should not be interpreted as limiting the scope or application of the present invention. The personal care absorbent article 10 includes a liquid permeable top sheet 12, a bottom sheet 14 and an absorbent core 16 disposed between the liquid permeable top sheet 12 and the bottom sheet 14. In this particular embodiment, a liquid management layer 18 is positioned between the top sheet 12 and the absorbent core 16.

In various embodiments, the top sheet 12 is designed to contact the wearer's skin and, therefore, preferably is soft to the touch while resisting abrasion. In various embodiments, the top sheet 12 is liquid pervious. Suitable materials for the top sheet 12 include, but are not limited to, a multiplicity of fibrous nonwoven webs such as bonded carded webs and more continuous fiber webs such as spunbond webs. Other suitable materials include liquid pervious films and laminates of films and/or nonwovens.

The bottom sheet 14 can be made from a variety of materials including, but not limited to, plastic films, fibrous nonwoven webs, foams and combinations of the foregoing including laminates. The main attribute of the bottom sheet 14 is that it retains any deposited solids or liquids that are received by the personal care absorbent article 10. As a result, it is generally desirable that the bottom sheet 14 be liquid impervious. In order to facilitate increased comfort, it also may be desirable to form the bottom sheet 14 such that it is breathable. Some materials such as fibrous nonwoven webs tend to be breathable by nature due to their construction. Other materials such as plastic films can be made breathable by aperturing and/or through the use of microporous films which oftentimes contain fillers. Such filler-containing films are either stretched or crushed to create pores adjacent the filler thereby providing a path through the film which will permit, for example, water vapor to be transmitted therethrough. Other films are available which transmit water vapor using diffusion mechanisms.

The absorbent core 16 can be disposed between the top sheet 12 and bottom sheet 14 and is used to absorb the main portion of the body fluids or other liquids delivered to it through the top sheet 12. The absorbent core may be made from a wide variety of materials including, but not limited to, natural and/or synthetic pulp, fluff fibers, hydrophilic thermoplastic fibers and/or thermoplastic fibers which have been treated to be hydrophilic. The absorbent core also may contain superabsorbents. Furthermore, these materials may be used alone or in combination. For example, wood pulp fluff may be used alone or in combination with a superabsorbent to increase the overall capacity of the absorbent core. In addition, more rigid thermoplastic fibers may be used to maintain the integrity of the absorbent core and to assist in preventing collapse of the absorbent core once it has become wetted.

The liquid management layer 18 can be positioned between the liquid permeable top sheet 12 and the absorbent core 16. The purpose of the liquid management layer 18 can be to further separate the absorbent core 16 from the surface or skin of the wearer in an effort to reduce liquid flow back from the absorbent core 16 to the top sheet 12. In the embodiment illustrated in FIG. 1, the liquid management layer 18 is positioned over the absorbent core 16. If desired, the liquid management layer 18 can be varied in size and thus can be made smaller or larger than the absorbent core 16. In addition, the liquid management layer 18 can be made to the same dimensions as the liquid permeable top sheet 12 thereby causing it to cover the entire absorbent core 16 and the bottom sheet 14.

In other embodiments, the top sheet 12 may be optional or omitted such that the liquid management layer 18 would be adjacent to the surface or skin of the wearer. In such an embodiment, the liquid management layer 18 is sized to cover the perimeter of the absorbent core 16, and preferably is sized to similar dimensions as the bottom sheet 14. In some embodiments, the liquid management layer may not have as soft a feel as is typically possible with respect to conventional top sheet materials in which case it may be desirable to place the liquid management layer underneath a separate top sheet 12 such as in the configuration illustrated in FIG. 1.

The liquid management layer according to the present invention may be used alone or in combination with other materials and/or layers either in a stacked configuration, or in a bonded or otherwise attached form, with one or more other layers of the personal care absorbent article. Generally, the layer closest to the surface of the wearer is typically attached or secured to the bottom sheet. It may be desirable to attach the liquid management layer 18 to one or more of the other layers or components of the personal care absorbent article 10 including, for example, the top sheet 12, the absorbent core 16 and/or bottom sheet 14.

The liquid management layer of the present invention includes a combination of properties such that when the liquid management layer is incorporated into a personal care absorbent article, the liquid management layer effectively absorbs and transfers liquid to the absorbent core as well as minimize the rewet of liquid to the surface of the wearer when placed under a compressive load such as when a baby wearing the diaper is in a sitting position. To this end, embodiments of the invention are directed to a liquid management layer that includes a plurality of thermoplastic fibers in the form of a spunbond nonwoven web, where the plurality of thermoplastic fibers are randomly oriented and uncrimped. The liquid management layer exhibits a maximum void volume of 25 cc/g and a web density of at least 0.05 g/cc. In various embodiments, the liquid management layer exhibits a maximum thickness of 1.5 mm, a basis weight of at least 30 g/m$^2$ and a rewet value of less than 0.4 g according to test method WSP 70.8 described in detail below. Additionally, in various embodiments, the liquid management layer has an average fiber diameter of at least 40 microns based on the number of thermoplastic fibers in the liquid management layer and wherein less than 10% by count of the plurality of thermoplastic fibers in the liquid management layer have an absolute diameter less than 30 microns.

This unique combination of fiber properties makes the liquid management layer particularly effective for use in personal care absorbent articles. The liquid management layer is produced by spunbond processing procedures making the manufacturing process economical. The liquid management layer exhibits dimensional stability such that the physical attributes of the material are not substantially effected by storage or winding tension during processing. Embodiments of the present invention are particularly well-suited for separating the absorbent core of a personal care absorbent article from the top sheet against the skin or surface of the wearer of such products.

Fibers in the Liquid Management Layer

In various embodiments, the thermoplastic fibers in the liquid management layer have an average diameter of at least 40 microns based on the number of thermoplastic fibers in the liquid management layer. In general, the number of fibers in the liquid management layer is determined by optical or microscopic inspection of a liquid management layer as discussed in the testing procedures section below. In some embodiments, the average fiber diameter of the plurality of thermoplastic fibers can range from 40 microns to 80 microns, or from 45 microns to 75 microns, or from 50 microns to 70 microns, or other range values. In still further embodiments, the average fiber diameter of the plurality of thermoplastic fibers can be at least 45 microns, or in other embodiments, can be at least 55 microns. The plurality of thermoplastic fibers can comprise, for example, at least 60%, or at least 70%, or at least 80%, or at least 90%, or at least 95%, or at least 99% up to 100%, or from 50% to 100%, or from 60% to 99%, or from 70% to 95%, or other range values by weight of the total fiber content of the spunbond nonwoven web. "Total fiber content" refers to fibers from all sources, including all continuous fibers and all staple fibers and all other fibers which may be present in the spunbond nonwoven web alone or in combinations.

In order to maintain the properties and characteristics of the liquid management layer, less than 10% by count of the plurality of thermoplastic fibers in the liquid management layer have an absolute fiber diameter less than 30 microns. In other embodiments, less than 5%, or less than 4%, or less than 3%, or less than 2% or less than 1%, of the thermoplastic fibers in the spunbond nonwoven web have an absolute diameter less than 30 microns. In various embodiments, at least 90%, or at least 95%, or at least 99% up to 100%, of all the thermoplastic fibers of the spunbond nonwoven web, exhibit an absolute fiber diameter of at least 30 microns or more, or at least 35 microns or more, or at least 40 microns or more. In various embodiments, these range values for absolute fiber diameters can apply to the total fiber content of the liquid management layer.

Fibers in the liquid management layer can be formed from thermoplastic material. Examples of suitable thermoplastic materials can include, but are not limited to, polyolefins, such as, polyethylene and/or polypropylene, as well as, polyesters, polyamides, and poly vinyl alcohol, as well as, homopolymers, copolymers and blends of the foregoing. The cross-sectional shape of the thermoplastic fibers may be either circular or non-circular. Although not limited thereto, the width of the thermoplastic fibers can be uniform or essentially uniform along the entire length of the fibers, wherein variations in the width can be, for example, less than about ±10%, or less than about ±5%, or less than about ±2%, or less than about ±1%, or from 0 to ±2%, or other values. The thermoplastic fibers are substantially continuous fibers formed in the spunbond process described below.

The fibers may be solid or hollow. In addition, they may be made from a single fiber polymer or from multiple polymers such as are found in multiconstituent and multicomponent fibers (collectively referred to as "multicomponent" fibers). Multicomponent fibers tend to have two or more polymers which are present in or deposited through-out the fiber. Multicomponent fibers tend to have two or more polymers present in distinct and separate areas most typically along the longitudinal axis of the fiber. Thus, using multicomponent fiber that are bicomponent, for example, fiber cross-sections may be sheath/core, side-by-side or islands-in-the-sea cross-sections. Typically, with such bicomponent fibers one of the polymers has a lower softening or melting point than the other polymer or polymers. This lower melting/softening polymer can often be present on at least a portion of the exterior or exposed surface of the fiber and is used to bond the fibers of the nonwoven web together. The liquid management layer of the present invention can be made from a single type of fiber or a blend of fibers such as, for example, a blend of polyethylene single component fibers and one or more bicomponent fibers such as polyethylene sheath/polypropylene core or polyethylene sheath/polyester core bicomponent fibers.

In order to achieve the specified structure and properties of the liquid management layer of the present invention, the thermoplastic fibers of the liquid management layer are uncrimped. Uncrimped fibers exhibit less than three crimps per extended inch. In some embodiments, uncrimped fibers exhibit no more than two crimps per extended inch, and in other embodiments, have no crimps in the fiber. As discussed above, crimping has been used in previous materials to increase the void volumes and loft of the materials. The liquid management layer of the present invention utilizes uncrimped fibers and results in a low loft material with low void volumes. Typically crimped fibers are meltspun thermoplastic fibers in which no mechanical crimping, latent crimping, and/or chemical crimping steps have been performed after formation of the fibers.

Thermoplastic fibers making up the liquid management layer of the present invention can be in the form of a spunbond nonwoven web. Spunbond nonwoven webs can be made from meltspun thermoplastic fibers which are formed by extruding a molten thermoplastic material as fibers from a plurality of fine capillaries in a spinneret. The diameter of the extruded fibers then can be reduced in diameter and deposited on a collecting surface in the form of a nonwoven web of continuous fibers. In various embodiments, thermoplastic fibers of the liquid management layer are continuous in that the fibers are produced in a spunbond process in which the continuously extruded fibers are deposited directly on the collector in the form of a nonwoven web. This is in contrast to nonwoven webs made from non-continuous fibers, such as thermoplastic staple fibers. In contrast to spunbond processing, the staple fibers are extruded and cut to specified lengths usually less than about 150 mm and then subsequently formed into a nonwoven web. The production of spunbonded nonwoven webs is illustrated in patents such as Appel et al., U.S. Pat. No. 4,340,563, Dorschner et al., U.S. Pat. No. 3,692,618; McKinney, U.S. Pat. Nos. 3,338,992 and 3,341,394; Hartmann, U.S. Pat. No. 3,502,763; Dobo et al., U.S. Pat. No. 3,542,615; Pike et al., U.S. Pat. No. 5,382,400; and Matsuki et al., U.S. Pat. No. 3,802,871, which are all incorporated herein by reference in their entirety.

In some embodiments, the liquid management layer can be constructed from one or more layers of spunbond nonwoven webs, provided that the liquid management layer maintains the structure and properties of the invention. For example, one or more beams of extruded fibers can be used to form the spunbond nonwoven web. Alternatively, two or more layers of a spunbond nonwoven web can be used for the liquid management layer.

The thermoplastic fibers of the liquid management layer can be randomly oriented in that the fibers do not exhibit a strong degree of orientation in the spunbond nonwoven web. An indication of the degree of orientation of the fibers in the spunbond nonwoven web is the ratio of the strip tensile strength in the machine direction to the strip tensile strength in the cross-machine direction (MD:CD). In certain embodiments, the MD:CD ratio of the spunbond nonwoven web for the liquid management layer is five or less, and preferably three or less. This is in contrast where fibers are lay down in a parallel fashion or, in contrast to carding process where the staple fibers are substantially aligned during the formation of the web and typically produce a MD:CD ratio greater than 5 if not cross lapped or combined with other webs in a way to compensate this strong anisotropy.

Properties of the Liquid Management Layer

As referenced above, a relevant property of the liquid management layer can be the void volume. The void volume of the liquid management layer is a measure or indication of the open structure of the fabric under low loads. The void volumes of the liquid management layer of the present invention are low when compared to the void volumes of typical liquid management layers. The liquid management layer of the present invention exhibits a maximum void volume of 25 cc/g. In other embodiments, the liquid management layer exhibits a maximum void volume of 20 cc/g. In further embodiments, the maximum void volume can range from about 7 cc/g to about 25 cc/g, or from about 10 cc/g to about 20 cc/g, or other values.

In various embodiments, the liquid management layer, which can be the spunbond nonwoven web alone or in combination with another layer(s), can exhibit a basis weight of at least 30 g/m$^2$. In some embodiments, the basis weight of the liquid management layer can be at least 40 g/m$^2$, or at least 60 g/m$^2$. In some embodiments, the basis weight of the liquid management layer can range from about 30 g/m$^2$ to about 100 g/m$^2$, or from about 35 g/m$^2$ to about 95 g/m$^2$, or from about 40 g/m$^2$ to about 90 g/m$^2$, or from about 50 g/m$^2$ to about 80 g/m$^2$, or other range values The density of the spunbond nonwoven web can be at least 0.05 g/cc and in some embodiments the web density can have a value ranging from 0.05 g/cc to 0.15 g/cc, or from 0.07 g/cc to 0.12 g/cc, or from 0.08 g/cc to 0.10 g/cc, or other values. The liquid management layer can exhibit a maximum thickness of 1.5 mm, and in some embodiments can be below 1 mm, in still additional embodiments can be below about 0.8 mm, and the thickness can range from about 0.1 mm to 1.5 mm, or from 0.25 mm to 1.25 mm, or from 0.5 mm to about 1 mm, or other range values.

Further, in some embodiments, the liquid management layer exhibits a permeability factor of at least 11, or at least 12, or at least 13, or at least 15, or at least 17, or other values. The permeability factor is related to the air permeability of the material and is normalized for the basis weight of the material. The permeability factor provides information pertaining to the open structure of the liquid management layer such that the larger the number, the more open the structure.

To be useful in a personal care absorbent article, the liquid management layer should be able to take in successive insults. This characteristic is generally referred to as strike through performance. EDANA/INDA Worldwide Strategic Partners standard test WSP 70.7 (05) "Standard Test Method for Nonwovens—Repeat Liquid Strike-Through time" ("WSP 70.7") is a standard method for evaluating the ability of a liquid management layer to handle multiple insults. The liquid management layer of the present invention exhibits a strike through performance according to test method WSP 70.7 of less than 1.7 seconds for the second insult and 1.9 seconds for the third insult.

In addition to handling multiple insults, the liquid management layer should exhibit liquid handling capabilities such as minimizing the rewet of liquid from the absorbent core back to the surface of the layer adjacent the wearer. EDANA/INDA Worldwide Strategic Partners standard test 70.8 (05) "Standard Test Method for Wetback After Repeated Strike-Through Time" ("WSP 70.8") is a standard method for evaluating the rewet performance of materials for use in personal care absorbent articles. The liquid management layer of the present invention exhibits a rewet value of less than 0.4 g according to test method WSP 70.8, and in some embodiments less than 0.3 g, and in other embodiments, less than 0.2 g.

The liquid management layer is resilient and does not exhibit a large degree of compression under load. The liquid management layer tends to resist compression under load thereby maintaining a spaced-apart relationship between the absorbent core and the skin or surface of the wearer. In addition, the liquid management layer exhibits a very open structure which does not readily retain liquids and promotes air circulation. Consequently, the material tends to provide separation between the absorbent core and the skin or surface of the wearer. If the liquid management layer is compressed, the material tends to exhibit compression resilience such that the pore structure of the liquid management layer does not substantially change upon compression, thereby maintaining its performance as a liquid management layer. In certain embodiments, the liquid management layer exhibits a maximum compressibility of 30%. In some embodiments, the maximum compressibility of the liquid management layer can be 20%, and in further embodiments can be 15%, or other values.

Once the spunbond nonwoven web has been formed, the web in some preferred embodiments then can be stabilized by one or more bonding methods. One bonding method is powder bonding wherein a powder adhesive is distributed through the web and is then activated by heating the web and adhesive with hot air. Another method when using multicomponent fibers is to use a through-air bonder which is well known in the art. In a through-air bonder, a flow of heated air is applied through the web to heat the web to a temperature above the melting or softening point of the lower melting component of the multicomponent fibers but below the melting or softening point of the higher melting component. Upon heating, the lower melting polymer portions of the web fibers are melted or softened and the melted/softened portions of the fibers adhere to adjacent fibers at the crossover points while the high melting polymer portions of the fibers tend to maintain the physical and dimensional integrity of the resultant nonwoven web. Typically the unbonded web is supported on a forming wire or drum. In addition, a vacuum may be pulled through the web if so desired to further contain the fibrous web during the bonding process. In some embodiments, a preferred bonding method is thermal point bonding where a heated calendar rolls or ultrasonic bonding equipment is used to bond fibers together in a localized bond pattern though the web. Typically, for a point bonded fabric, the setup includes passing the nonwoven web to be bonded between at least two calender rolls. One of the calender rolls has a smooth surface, while the second calender roll has a raised pattern on the surface. The calender rolls are maintained at a temperature such that when the nonwoven web is passed through the calender rolls, pressure is applied to the nonwoven web and the fibers of the nonwoven web are at least partially bonded when pressed against the smooth calender roll by the raised portions of the patterned calender roll. The bonding patterns can have different sizes, shapes, and orientation. Most common point bonding pattern is a repeating pattern of small diamonds. For ultrasonic bonding, the nonwoven web is passed between a patterned roll and an ultrasonic horn oscillating at high frequency which compresses the thermoplastic fibers against the raised pattern and causes the fibers to soften and form a bond between the fibers. The bonding area for thermal or ultrasonic point bonding may range from about 5% to about 30%.

It is desirable that the liquid management layer be at least somewhat hydrophilic in order to aid in the transfer of liquid to the absorbent core. Hydrophilic describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials are well known in the art. Fibers having contact angles less than 90° are designated "wettable" or hydrophilic, while fibers having contact angles equal to or greater than 90° are designated "nonwettable" or hydrophobic.

Some fibers are naturally hydrophilic. Other fibers such as polyolefins tend to be hydrophobic and therefore typically require a surface treatment in order to increase their hydrophilicity. Wetting agents/surfactants may be added either internally, such as with siloxane during the fiber formation process or externally as a post treatment either to the fibers and/or the resultant web as with anionic and nonionic surfactants. Silastol 163 or Silastol PST, both from Schill+Seilacher GmbH, are examples of surfactants which can be used to increase the hydrophilicity of a fibrous nonwoven web. Suitable wetting agents/surfactants as well as their use are well-known and need not be described herein in detail. While it is desirable that the fibrous nonwoven web be somewhat hydrophilic, it is less desirable to increase the hydrophilicity to such an extent that the material tends to retain liquid and provide a wet contact surface for the skin of the wearer. Therefore, it may be necessary to adjust the degree of hydrophilicity up or down to optimize this criterion.

The liquid management layer of the present invention may be used in a wide variety of applications including, but not limited to, personal care absorbent products including, for example, diapers, training pants, incontinence devices, sanitary napkins, and the like. Generally in such applications, the liquid management layer can be associated with the portion of the personal care absorbent product which is located on the side of the absorbent core which faces the wearer and may be used with or without a top sheet or it can be positioned between the top sheet and the absorbent core or it can form a portion of the top sheet or the absorbent core in the form of a composite which may or may not be laminated as, for example, by thermal or ultrasonic bonding, adhesives, needling, stitching and hydroentangling. It is also possible to use the material according to the present invention across the entire surface of the product or it can be used in select locations which may or may not be spaced apart from one another.

The following series of tests are set forth for the purpose of measuring the herein-described parameters. In addition to the test procedures set forth below, a series of examples are also presented. The examples are provided to illustrate various embodiments and highlight certain features of the present invention and should not limit the scope of the invention in any way.

TEST METHODS

Thickness

Thickness or caliper data were obtained by measuring a single layer of the liquid management layer or the spunbond nonwoven using an Ames gauge tester model 91-013 fitted with ADP-1116 head and a circular foot covering an area of 12.6 square centimeter (1.95 square inch). For those measurements, the gauge was used with no additional weight and the pressure exercised by the foot was measured at 0.41 KPa (0.06 psi).

Compressibility

Compressibility data were obtained by measuring a single layer of the liquid management layer or the spunbond nonwoven using a CSI-55 gauge tester manufactured by Custom Scientific Instrument, Newark, N.J. USA. The tester was fitted with a 6.45 square centimeter (1 square inch) circular foot. This tester was used with either no weight, a 2 ounce weight, or a 6 ounce weight. Under those conditions it was calculated that the foot applied respectively pressures of 215, 1077 and 2800 Pa (As per the specification of the gauge tester, with no weight the foot apply a force of 215 Pa or 0.5 ounce).

Void Volume

Void volume (VO) is the amount of void space in the spunbond fabric in cubic centimeter per gram of fabric when the thickness of the spunbond is measured under pressure of 0.41 KPa (0.06 psi). Void volume is calculated from the measurement of thickness, the basis weight of the spunbond fabric and the density of the polymer forming the fibers. For polypropylene fibers a density of 0.905 g per cubic centimeter was used. The equation for calculating void volume (VO) can be expressed as follows:

$$VO=V1-V2/BW$$

where, V1 is the volume for one (1) square meter of spunbond expressed in cubic centimeters, and is calculated from the thickness measurement T1 as follows:

V1=10,000*T1, where T1 is the spunbond thickness expressed in mm,

V2 is the volume occupied by the fibers and can be calculated using the following formula:

$$V2=BW/D$$

Where, BW is the basis weight of the spunbond nonwoven web in gram per square meter and D is the density of the polymer in gram per cubic centimeter.

For the void volume data presented herein, the web thickness measurements were made according to the thickness test method described above using the Ames model 91-013 tester fitted with the ADP1116 head, the 12.6 square centimeter circular foot and at a load of 0.41 KPa.

Air Permeability

Air permeability data were produced using a TexTest FX3300 Air Permeability Tester manufactured by TexTest AG, Zurich, Switzerland. The tester was used accordingly with the manufacturer instructions. The reading were obtained with a 38 mm orifice and a pressure drop of 125 Pa for all samples, except for samples 2, 5 and 15 where an orifice of 20 mm was used. Readings were made on a single ply of the samples at a time.

Air Permeability Factor

Air permeability factor (APF) is defined as the air permeability in cubic meter per square meter per minutes ($m^3/m^2/min$) multiplied by the basis weight of the substrate being tested in grams per square meter and divided by 1000. Air permeability values can vary depending upon the basis weight of the sample. The air permeability factor normalizes the samples of different basis weights and allows for a more direct comparison of the permeability between samples of different basis weights. Air permeability factor can be represented by, $$APF=AP*BW/1000 \text{ where,}$$

AP is the air permeability of the substrate in $m^3/m^2/min$, and

BW is the basis weight in grams per square meter.

Web Density

Web density (WD) is expressed in cubic centimeter per gram and, it is calculated from the web thickness measured under a load of 0.41 KPa as described above and the basis weight of the sample according to the following formula:

$$WD = T1*1000/BW$$

where, T1 is thickness of the web in mm and BW is basis weight of the web in grams per square meters, g/m².

Web Porosity

Web Porosity (Po) is expressed as a percentage and, it is calculated as follows:

$$Po = 100*[1-(WD/FD)] \text{ where,}$$

WD is web density in cubic centimeter per gram and FD is fiber density expressed in grams per cubic centimeter. For polypropylene fibers, 0.905 gram per cubic centimeter is used as the value of FD.

Strip Tensile Strength

The strip tensile strength of the web is measured according to Worldwide Strategic Partners standard test method WSP 110.4 (05) option B with the exception that the initial jaw separation was 100 mm rather than 200 mm as specified in the method. The sample strips are 5 cm wide and the rate of separation is 100 mm/min. The test was performed on strips of spunbond or liquid management layer cut in direction parallel to the machine direction (MD) and the transverse or cross direction (CD) of the web. The MD and CD strip tensile ratio (STR) is defined as:

$$STR = ST_{MD}/ST_{CD} \text{ where,}$$

$ST_{MD}$ is the strip tensile strength for the strips having their long direction parallel with the machine direction of the sample web and, $ST_{CD}$ is the strip tensile strength for the strips having their long direction parallel with the cross direction of the web.

WSP Multiple Strike Through and Rewet

Strike through and rewet data were obtained by testing the samples as per EDANA/INDA Worldwide Strategic Partners standard tests WSP 70.7 (05) "Standard Test Method for Nonwovens—Repeat Liquid Strike-Through time" ("WSP 70.7") and 70.8 (05) "Standard Test Method for Wetback After Repeated Strike-Through Time" ("WSP 70.8"). The WSP 70.7 tests were performed using a Lister AC by Lenzing Instruments GmbH & Co KG, Lenzing, Austria. For the WSP 70.7 test method, the strike through time for insult of 5 ml of a 0.9% saline solution was recorded in seconds after the first, second and third insult. After performing the WSP 70.7 test on a sample, rewet was measured in accordance with WSP 70.8. For the WSP 70.8 test method, the WetBack testing unit from Lenzing Instruments GmbH & Co was used. Paper used for the absorbent core was type ERT FF3 supplied by Hollingworth & Vose, Winchcombe, England. The filter paper used for rewet test was the type ERTMWWSSHEETS, 125 mm (UPC 0041729020442) also from Hollingworth & Vose.

The target for an acceptable liquid management layer is to achieve strike through times measured according to test method WSP 70.7 that are less than 1.7 seconds for the second insult and 1.9 seconds for the third insult. The target for rewet as measured according to test method WSP 70.8 is to be equal or less than 0.2 gram.

Diaper Simulation Strike Through and Rewet

Diaper Simulation Strike Through and Rewet method is a comparative testing method utilizing a commercial baby diaper as the absorbent article chassis. The commercial baby diapers used were sold by Target Corporation as the "UP & UP" store brand and, they were bought during the first 9 months of 2010. The product used was size 4 and was identified by the code DPCI 007-01-0049.

For this test, the diaper topsheet was unglued on one side using a hot air gun, the original liquid management layer was removed and replaced by the liquid management layer to be tested. The topsheet was repositioned prior to the testing. The apparatus used for the testing consisted of a test block weighting 3.6 Kg (8 lb) and having a based that is 101 mm×101 mm (4 inches×4 inches) The test block includes a cylindrical shape throughbore. The insults are applied to the sample through the cylindrical shaped throughbore. The test block is built on the same general principle as the test block used for WSP 70.7, except the dimensions are different. The solution used for this test consists of a 1% by weight solution of sodium chloride in deionized water. The strike through block (STB) is positioned over the reassembled diaper with the hole centered in the geometrical middle of the liquid management layer. A first insult of 80 ml is poured and the time is recorded for complete absorption based on lost of contact between the electrodes built-in the STB.

After 10 minutes, a second insult of same size is poured and the second strike through time is recorded. After another 10 minutes, the STB is removed and 16 weighted filter paper (VWR North American Cat. No. 28313-057, 9 cm Filter paper qualitative #417) are placed against the topsheet, centered on the target zone. Then, a 101 mm×101 mm rewet block (RWB) weighting 3.6 Kg (8 lb) having foam padding affixed to surface used to press against the sample which is covered by an impermeable film is placed over the assembly on top of a stack of filter paper. The RWB is left in place for 2 minutes after which the RWB is removed and the stack of filter paper is weighted. The difference between the weight of the stack of filter papers before and after the contact with the diaper is the rewet in gram. Within 30 second after removing the stack of filter paper, the STB is repositioned and a third insult is applied to the diaper. After 10 minutes the rewet test is repeated.

Fiber Diameter

Measuring the average fiber diameter of fibers in the range between 10 and 100 microns (i.e., μm or micrometers) in a nonwoven material is a common test for those knowledgeable in the art. It typically involves microscopic inspection of the sample. For this test, typically 3 representative pieces are taken across the width of the web. Each piece is examined using a microscope and looking at the piece with the observer positioned at 90 degree angle from the plane of the piece. Using typical method known to measure distance between two points in the field of view of a microscopic image, the width of randomly selected fibers is measured. Those fiber widths are typically recorded to the nearest 0.1 micron. It is assumed by this method that the fiber width is equal to the fiber diameter for both round and non-round fibers.

This measurement can be performed with an optical microscope or a scanning electron microscope as long as they are calibrated using an acceptable standard (e.g. Optical grid calibration slide 03A00429 S16 Stage Mic 1MM/0.01 DIV from Pyser-SGI Limited, Kent, UK or SEM Target grid SEM NIST SRM 4846 #59-27F). A common method to select fibers at random is to measure the width of fibers along a line between two points set across the piece being examined. This approach minimizes multiple measurements of the same fiber. Typically, to determine the average diameter of the fibers, a minimum of 30 fibers are measured among the pieces examined for a given sample. The average is calculated based on the count of the fibers. In other words, each fiber measurement is given the same weight of 1 in the calculation of the average (e.g., if the diameters of 30 fibers were measured, and the measurements were 5 fibers at 30 microns, 10 fibers at 40 microns, and 15 fibers at 50 microns, then the "average diameter" of the fibers would be determined to be 43 microns ($100\times[((5\times30)+(10\times40)+(15\times50))/30]$). For determining the percentage of fibers having an absolute diameter less than 30 microns, the minimum number of fibers measured is at least 300. The percentage is also calculated using a count basis. For example, if 30 out of 300 measured fibers had a measured diameter of less than 30 microns, then the percentage of fibers of the spunbond nonwoven web considered to have an absolute diameter less than 30 microns would be 10% ($30/300\times100$). Determinations of the percentage of fibers having an absolute diameter greater than or equal to 30 microns, or other values, can be conducted similarly.

EXAMPLES

Samples 1-14 of point bonded spunbond described below were made using a single beam spunbond line with point bonding capabilities. The continuous fibers were produced using a spin beam manufactured by Reifenhauser GmbH & Co. KG and commonly referred to as Reicofil 2. The spinneret had capillaries with a diameter of about 2 mm. The capillaries in the die had a round cross-sectional shape and, the cross-section of the continuous fibers produced was also substantially round. The molten polypropylene polymer was extruded through those capillaries at a rate of about 0.93 gram per capillary per minutes (also commonly referred to as ghm). While maintaining the throughput, melt temperature and dimensions of the draw channel constant, the diameter of the fibers was varied by adjusting the volume of suction air (i.e. air removed from under the belt) and the volume of cooling air (the volume of air fed to the pressurized cooling chamber). This volume of cooling air strongly affect the velocity of the air traveling down the draw channel, which in turn, strongly affect the downward force applied to the fiber being spun.

The calender used for bonding the fabric was equipped with heated rolls, one being smooth and the other being engraved with a diamond pattern. The bonding area produced by this calender covered about 13.5% of the fabric. The pressure applied by the calender rolls was kept constant while their temperature was adjusted as commonly done based on the weight of the fabric to be bonded, reflecting that a heavier fabric needs a higher temperature than a light fabric to achieve near optimum bond strength. The samples 15-17 were produced on a commercial spunbond production line of similar design to the one described above and also equipped with a Reicofil 2 spin beam. The spin beam was equipped with a spinneret having capillaries with a diameter of 2 mm. For those samples, the throughput was within a range of 0.8 to 0.95 ghm. The bonding area produced by this calender was between 15 and 19%.

Those samples were made using isotactic polypropylene homopolymer. Polypropylene polymers having nominal Melt Flow Rate of 6, 8 or 12 MFR were used (MFR being measured by ASTM D1238 at temperature of 230° C. and using a 2.16 Kg weight).

By selecting the polymer as well as the process conditions that influenced the drawing of the continuous fibers, samples were made with different average fiber diameter. Samples of different basis weight were made by changing the speed of the belt on which the filaments were deposed.

To render the sample hydrophilic or wettable, a commercial treatment process was simulated by immersing the samples into aqueous solution containing 0.2% by volume of Silastol 163, a finish commercialized by Schill+Seilacher GmbH and used to confer hydrophilic characteristic to nonwovens. The samples after soaking were wrung twice using an Atlas Laboratory Wringer Model LW-1 set with weights that totaled about 1.5 Kg. Subsequently the samples were dried in an air circulated oven at about 70° C. Before testing, the treated samples were left at room temperature for at least one hour.

Samples 1, 2, 3 and 4

Samples 1-4 were made using the 8 MFR isotactic homopolymer polypropylene resin at process conditions that produced continuous fibers with average diameter of 66 microns. Belt speeds were selected to produce samples at the basis weight of about 18, 30, 40 and 60 $g/m^2$.

Comparative Sample 5

Samples 5 was made with the 8 MFR isotactic homopolymer polypropylene resin at process conditions that 6 produced continuous fibers with an average diameter of about 48 microns. Belt speed was selected to produce samples at basis weight of about 18 $g/m^2$.

Samples 6, 7, and 8

Samples 6-8 were made with the 8 MFR isotactic homopolymer polypropylene resin at process conditions that produced continuous fibers with an average diameter of about 48 microns. Belt speeds were selected to produce samples at basis weight of about 40, 50 and 60 $g/m^2$.

Samples 9, 10 and 11

Samples 9-11 were made with the 12 MFR isotactic homopolymer polypropylene resin at process conditions that produced on average continuous fibers with an average diameter of about 43 microns. Belt speeds were selected to produce samples at basis weight of about 40, 50 and 60 $g/m^2$.

Comparative Samples 12, 13 and 14

Samples 12-14 were made with the 12 MFR isotactic homopolymer polypropylene resin using process conditions that produced continuous fibers at an average diameter of about 31 microns. Belt speeds were selected to produce samples at basis weight of about 40, 50 and 60 $g/m^2$.

Samples 15, 16 and 17

Samples 15-17 were made with a 6 MFR polypropylene resin on a commercial production line that is very similar in design to the one used for sample 1 to 14. Belt speeds were selected to produce a basis weight of about 30, 75 and 95 $g/m^2$. The process conditions were set to respectively produce average fiber diameter of 50, 57 and 54 microns.

Comparative Sample 18

This sample is fabric type 4191. It is a commercial product made by Polymer Group Inc., Charlotte, USA, and has been marketed mainly as a liquid management layer for used in hygienic personal care absorbent products. That fabric has a nominal basis weight of about 42 $g/m^2$. It is a fabric that mainly comprises a blend of staple bicomponent crimped fibers that have been carded into a web and stabilized by through-air bonding. The fiber blend used consists of 6 and 12 dpf fibers having a core made of polyester and a sheath made of polyethylene.

Comparative Sample 19

This sample is fabric type 4194 is a commercial product made by Polymer Group Inc. and has been marketed mainly as a liquid management layer for use in hygienic absorbent products. That fabric has a nominal basis weight of about 35 $g/m^2$. Like 4191, it is a fabric that mainly comprises a blend of staple bicomponent crimped fibers that have been carded into a web and stabilized by through-air bonding.

Physical properties of samples 1-18 were measured and reported in Table 1. The strike through and rewet characteristics for samples 2-15 and 18 were performed according to WSP 70.7 and 70.8 Multiple Strike Through and Rewet tests and the data are reported in Table 2. The data in Table 2 illustrates that samples 2, 3, 4, 6, 7, 8, 9, 10, 11 and 15 performed well with strike through and rewet. The values for these samples were less than or equal to 0.2 grams for rewet, and the second strike through for these samples was less than 1.7 seconds, and third strike through less than 1.9 seconds. Comparative sample 18 is a traditional high loft liquid management layer which performed well, as expected. Samples 2, 3, 4, 6, 7, 8, 9, 10, 11 and 15 performed unexpectedly well in view of their low thickness and associated low void volume. In contrast, samples 5, 12, 13 and 14 did not exhibit the combination of properties of the invention and thus did not perform even though the thickness and void volume were low. The basis weight of sample 5 was at 18 g/m² which is below that of the present invention. The average fiber diameter for comparative samples 12, 13 and 14 was 31 microns which is below that for the invention.

Samples 2-4 and 6-11 and 18 were tested according to the Diaper Simulation Strike Through and Rewet test using a diaper chassis and reported in Table 3. The data in Table 3 follows the same general trends as identified by the more standard WSP 70.7 and 70.8 test methods reported in Table 2.

It was surprising that several of the spunbonds nonwoven webs made from continuous and uncrimped fibers having an average diameter equal or greater than 43 microns, a void volume of 25 cc/g or less, a basis weight of at least 30 g/m², and a thickness of 1.5 mm or less performed well in WSP 70.7 and 70.8 tests. This is surprising in view of the low thickness and void volume values of the material. For example, comparative sample 18 exhibited a void volume greater than 55 cc/g and a thickness of 2.6 mm.

It is commonly viewed that a liquid management layer should allow storage and rapid flow of the liquid through liquid management layer as well as within the plane of the layer. It is also commonly accepted that a liquid management layer also should avoid retaining moisture after the insult and, should provide a good barrier that prevents liquid from migrating back from the absorbent core when under load.

In regard to the relationship between fiber size and acquisition rate, without intending to be bound by the theory, it is believed that the smaller diameter of the uncrimped continuous fibers forming the samples 12, 13 and 14 produced web with smaller pores and smaller channels, therefore restricting the flow of liquid in the Z direction (out of plane toward the absorbent core) as well as restricting the flow of liquid though the in-plane direction (x-y direction) of the layer which resulted in the long acquisition rates. In contrast, samples 2-4, 6-11, and 15-17, utilized uncrimped fibers having diameter of 40 microns or larger which produced nonwoven webs with macro pores and channels that allowed for rapid distribution of the liquid through the layer in the z direction towards the absorbent core and through the x-y in-plane direction of the liquid management layer. Further, by comparing the samples of similar basis weights, it became clear that faster strike through values appears to correlate with larger diameter fibers. Another comparison is the performance in regard to strike through (WSP 70.7) with the permeability factor displayed in table 4. The results suggest that for spunbonds made from uncrimped filament and at or above 30 g/m² in basis weight, acceptable strike through is achieved for samples having a permeability factor of 11 or greater. Without intending to be bounded by the theory, it is believed this may be due to the permeability factor reflecting the apparent openness of the fabric. Also, the permeability factor generally increases with fiber diameter for spunbond made from uncrimped fibers.

Again, without being bounded by the theory, it is believed that the poor performance of sample 5 in regard to strike through reflects the lack of channels allowing rapid distribution of the liquid within the plane of the fabric. This suggests that there is a minimum coverage of large diameter uncrimped fibers that are needed to allow this type of fabric to perform as a liquid management layer. Sample 5 also performed poorly in rewet, again suggesting that the coverage of the large diameter uncrimped fibers was not good enough. Without intending to be bound by theory, it is believed that there were too many large pores allowing contact between the filter paper and the absorbent core, therefore allowing migration of liquid out of the absorbent core.

Another concern with traditional liquid management layers is the liquid retained in the structure of the liquid management layer. This is a common concern with high loft fabrics as the liquid droplets contained in the liquid management layer may not get in contact with the more hydrophilic absorbent core such that the liquid drop is not transferred to the absorbent core and is retained in the high loft liquid management layer. Liquid retention is much less of a concern with the liquid management layer of the present invention due to the open structure created by the large diameter fibers in the liquid management layer as reflected by the air permeability factor. The open structure of the liquid management layer promotes contact of the liquid droplets with the absorbent core thus promoting liquid transfer to the absorbent core.

Compressibility is provided in Table 5 for samples 1-17 and comparative samples 18 and 19. The compressibility of samples 1-17 was significantly less than the compressibility of the more traditional liquid management layers in comparative samples 18 and 19. Samples 1-17 exhibited compressibility values of 16% or less (at 2800 Pa) while comparative samples 18 and 19 were as high as 53%. (at 2800 Pa).

TABLE 1

| Sample | Basis Weight g/m² | Thickness mm | Air Permeability m³/m²/min | Fiber diameter micron |
|---|---|---|---|---|
| 1 | 19.3 | 0.33 | 749 | 66 |
| 2 | 37.2 | 0.52 | 496 | 66 |
| 3 | 48.6 | 0.58 | 381 | 66 |
| 4 | 57.7 | 0.68 | 356 | 66 |
| 5 | 18.0 | 0.31 | 685 | 48 |
| 6 | 38.6 | 0.54 | 354 | 48 |
| 7 | 48.3 | 0.55 | 295 | 48 |
| 8 | 60.7 | 0.60 | 235 | 48 |
| 9 | 37.0 | 0.45 | 334 | 43 |
| 10 | 48.1 | 0.52 | 262 | 43 |
| 11 | 59.7 | 0.60 | 214 | 43 |
| 12 | 40.2 | 0.49 | 225 | 31 |
| 13 | 50.3 | 0.52 | 176 | 31 |
| 14 | 57.5 | 0.56 | 176 | 31 |
| 15 | 30.2 | 0.44 | 428 | 50 |
| 16 | 73.0 | 0.69 | 212 | 57 |
| 17 | 94.9 | 0.78 | 146 | 54 |
| 18 | 41.4 | 2.64 | 410 | ~37(1) |

(1)Based on weight average of the fibers in the blend

TABLE 2

| Sample | Basis Weight g/m² | Avg. Fiber diameter micron | WSP 70.7 Strike through (sec) | | | WSP 70.8 Rewet G |
|---|---|---|---|---|---|---|
| | | | 1st insult | 2nd insult | 3rd insult | |
| 2 | 37.2 | 66 | 1 | 1.4 | 1.5 | 0.1 |
| 3 | 48.6 | 66 | 0.85 | 1.1 | 1.2 | 0.09 |
| 4 | 57.7 | 66 | 0.85 | 1.1 | 1.2 | 0.1 |
| 5 | 18.0 | 48 | 1.3 | 2.0 | 2.0 | 0.9 |
| 6 | 38.6 | 48 | 0.95 | 1.5 | 1.6 | 0.1 |
| 7 | 48.3 | 48 | 0.95 | 1.5 | 1.6 | 0.1 |

TABLE 2-continued

|  |  |  | WSP 70.7 Strike through (sec) |  |  |  |
|---|---|---|---|---|---|---|
| Sample | Basis Weight g/m² | Avg. Fiber diameter micron | 1st insult | 2nd insult | 3rd insult | WSP 70.8 Rewet G |
| 8 | 60.7 | 48 | 1.0 | 1.45 | 1.65 | 0.11 |
| 9 | 37.0 | 43 | 0.95 | 1.6 | 1.8 | 0.1 |
| 10 | 48.1 | 43 | 1.5 | 1.55 | 1.75 | 0.1 |
| 11 | 59.7 | 43 | 0.85 | 1.55 | 1.75 | 0.08 |
| 12 | 40.2 | 31 | 1.1 | 1.9 | 2.15 | 0.11 |
| 13 | 50.3 | 31 | 1.0 | 1.85 | 2.2 | 0.1 |
| 14 | 57.5 | 31 | 1.0 | 1.7 | 2.0 | 0.08 |
| 15 | 30.2 | 50 | 1.0 | 1.5 | 1.5 | 0.19 |
| 18 | 41.4 | — | 0.9 | 0.95 | 0.95 | 0.12 |

TABLE 3

Diaper Simulation Strike Through and Rewet

|  | Strike Trough (sec) |  |  | Rewet after 2nd insult g | Rewet after 3rd insult g |
|---|---|---|---|---|---|
| Sample | 1st insult | 2nd insult | 3rd insult |  |  |
| 2 | 32 | 33 | 40 | 0.18 | 0.7 |
| 3 | 30 | 30 | 34 | 0.14 | 1.0 |
| 4 | 28 | 27 | 30 | 0.16 | 0.5 |
| 6 | 39 | 38 | 50 | 0.06 | 0.7 |
| 7 | 34 | 37 | 38 | 0.15 | 1.0 |
| 8 | 36 | 37 | 44 | 0.07 | 0.5 |
| 9 | 44 | 46 | 54 | 0.07 | 0.9 |
| 10 | 35 | 36 | 38 | 0.13 | 1.1 |
| 11 | 38 | 40 | 48 | 0.19 | 0.3 |
| 18 | 22 | 23 | 26 | 0.28 | 1.0 |

TABLE 4

| Sample | Avg. Fiber diameter Micron | Void Volume cc/g | Permeability Factor | Web density g/cc | Porosity % |
|---|---|---|---|---|---|
| 1 | 66 | 16.8 | 14.7 | 0.056 | 94% |
| 2 | 66 | 12.9 | 18.5 | 0.072 | 92% |
| 3 | 66 | 11.0 | 18.5 | 0.083 | 91% |
| 4 | 66 | 10.5 | 20.5 | 0.086 | 90% |
| 5 | 48 | 16.1 | 12.3 | 0.069 | 92% |
| 6 | 48 | 13.3 | 13.7 | 0.086 | 90% |
| 7 | 48 | 10.5 | 14.3 | 0.095 | 89% |
| 8 | 48 | 9.4 | 14.3 | 0.058 | 94% |
| 9 | 43 | 11.4 | 12.4 | 0.080 | 91% |
| 10 | 43 | 10.2 | 12.6 | 0.088 | 90% |
| 11 | 43 | 9.4 | 12.8 | 0.095 | 89% |
| 12 | 31 | 11.0 | 9.0 | 0.083 | 91% |
| 13 | 31 | 9.2 | 8.9 | 0.097 | 89% |
| 14 | 31 | 8.6 | 10.1 | 0.103 | 89% |
| 15 | 50 | 13.5 | 16.9 | 0.069 | 92% |
| 16 | 57 | 8.3 | 15.5 | 0.106 | 88% |
| 17 | 54 | 7.1 | 13.9 | 0.122 | 87% |
| 18 | 37(1) | 58 | 9.9 | 0.017 | 98% |

(1)Average diameter calculated from weight average of the fibers forming the blend

TABLE 5

| COMPRESSABILITY | | | | | |
|---|---|---|---|---|---|
|  | Caliper of sample tested under load of: | | | Percentage compression | |
| Sample | 215 Pa | 1077 Pa | 2800 Pa | 1077 Pa | 2800 Pa |
| 1 | 0.33 | 0.30 | 0.28 | 7% | 15% |
| 2 | 0.47 | 0.44 | 0.41 | 6% | 12% |
| 3 | 0.59 | 0.56 | 0.53 | 6% | 10% |
| 4 | 0.65 | 0.62 | 0.59 | 5% | 10% |
| 5 | 0.31 | 0.30 | 0.28 | 6% | 11% |
| 6 | 0.53 | 0.50 | 0.48 | 5% | 9% |
| 7 | 0.55 | 0.52 | 0.50 | 5% | 9% |
| 8 | 0.57 | 0.55 | 0.52 | 4% | 9% |
| 9 | 0.44 | 0.43 | 0.40 | 3% | 10% |
| 10 | 0.49 | 0.47 | 0.44 | 5% | 10% |
| 11 | 0.59 | 0.56 | 0.53 | 5% | 10% |
| 12 | 0.44 | 0.42 | 0.39 | 5% | 10% |
| 13 | 0.50 | 0.48 | 0.47 | 4% | 7% |
| 14 | 0.55 | 0.54 | 0.52 | 3% | 7% |
| 15 | 0.44 | 0.40 | 0.37 | 8% | 16% |
| 16 | 0.72 | 0.70 | 0.67 | 4% | 8% |
| 17 | 0.83 | 0.81 | 0.78 | 3% | 7% |
| 18 | 1.69 | 1.23 | 0.80 | 27% | 53% |
| 19 | 1.70 | 1.21 | 0.80 | 28% | 53% |

Having described various embodiments of the invention in detail, it should be readily apparent that various other modifications and changes can be made in the present invention with departing from the spirit and scope of the following claims.

What is claimed is:

1. A liquid management layer for a personal care absorbent article, the liquid management layer comprising:
a plurality of thermoplastic fibers in the form of a spunbond nonwoven web, wherein the plurality of thermoplastic fibers are randomly oriented and uncrimped, wherein the liquid management layer has a maximum void volume of 25 cc/g and a web density of at least 0.05 g/cc, wherein the liquid management layer has a maximum thickness of 1.5 mm, a basis weight of at least 30 g/m² and a rewet value of less than 0.4 g according to test method WSP 70.8, and wherein the liquid management layer has an average fiber diameter of at least 40 microns based on the number of thermoplastic fibers in the liquid management layer and wherein less than 10% by count of the plurality of thermoplastic fibers in the liquid management layer have an absolute fiber diameter less than 30 microns.

2. The liquid management layer of claim 1, wherein the liquid management layer exhibits a maximum compressibility of 30%.

3. The liquid management layer of claim 1, wherein the fibers comprise polypropylene, and wherein all of the fibers in the liquid management layer are in the spunbond nonwoven web.

4. The liquid management layer of claim 1, wherein the liquid management layer exhibits a basis weight between about 30 g/m² to about 100 g/m².

5. The liquid management layer of claim 1, wherein the fibers exhibit an average fiber diameter ranging from about 40 to about 80 microns.

6. The liquid management layer of claim 1, wherein the average fiber diameter is at least 45 microns.

7. The liquid management layer of claim 1, wherein the average fiber diameter is at least 55 microns.

8. The liquid management layer of claim 1, wherein the spunbond nonwoven web is stabilized by thermal point bonding.

9. The liquid management layer of claim 1, wherein the liquid management layer exhibits a permeability factor of at least 11.

10. The liquid management layer of claim 1, wherein less than 5% by count of the plurality of thermoplastic fibers in liquid management layer have an absolute fiber diameter less than 30 microns.

11. The liquid management layer of claim 1, wherein at least 95% of the plurality of thermoplastic fibers in the liquid management layer have an absolute fiber diameter of at least 30 microns.

12. The liquid management layer of claim 1, wherein the fibers comprise polypropylene, and wherein the liquid management layer exhibits a basis weight at least 40 g/m² and is stabilized by thermal point bonding, and wherein the liquid management layer exhibits a maximum compressibility of 30% and a permeability factor of at least 11.

13. The liquid management layer of claim 1, wherein the average fiber diameter is at least 55 microns, wherein the fibers comprise polypropylene, wherein the liquid management layer exhibits a basis weight of at least 40 g/m² and is stabilized by thermal point bonding, and wherein the liquid management layer exhibits a maximum compressibility of 30% and a permeability factor of 11 or greater.

14. A personal care absorbent article comprising:
a bottom sheet, a liquid management layer, and an absorbent core positioned between the liquid management layer and the bottom sheet, wherein the liquid management layer comprises a plurality of thermoplastic fibers in the form of a spunbond nonwoven web, wherein the plurality of thermoplastic fibers are randomly oriented and uncrimped, wherein the liquid management layer has a maximum void volume of 25 cc/g and a web density of at least 0.05 g/cc, wherein the liquid management layer has a maximum thickness of 1.5 mm, a basis weight of at least 30 g/m² and a rewet value of less than 0.4 g according to test method WSP 70.8, and wherein the liquid management layer has an average fiber diameter of at least 40 microns based on the number of thermoplastic fibers in the liquid management layer and wherein less than 10% by count of the plurality of thermoplastic fibers in the liquid management layer have an absolute fiber diameter less than 30 microns.

15. The personal care absorbent article of claim 14, further comprising a top sheet, wherein the liquid management layer is positioned between the top sheet and absorbent core.

16. The personal care absorbent article of claim 14, wherein the average fiber diameter is at least 45 microns.

17. The personal care absorbent article of claim 14, wherein the average fiber diameter is at least 55 microns.

18. The personal care absorbent article of claim 14, wherein less than 5% of the plurality of thermoplastic fibers in the liquid management layer have an absolute fiber diameter less than 30 microns.

19. The personal care absorbent article of claim 14, wherein at least 95% of the plurality of thermoplastic fibers in the liquid management layer have an absolute fiber diameter of at least 30 microns.

20. The personal care absorbent article of claim 14, wherein the fibers comprise polypropylene, wherein the liquid management layer exhibits a basis weight at least 40 g/m² and is stabilized by thermal point bonding, and wherein the liquid management layer exhibits a maximum compressibility of 30% and a permeability factor of at least 11.

* * * * *